(12) United States Patent
Lerch et al.

(10) Patent No.: US 10,548,482 B2
(45) Date of Patent: Feb. 4, 2020

(54) MEDICAL IMAGING APPARATUS WITH A LIGHT SOURCE FOR ILLUMINATING AN EXAMINATION REGION

(71) Applicant: Siemens Healthcare GmbH, Erlangen (DE)

(72) Inventors: Daniel Lerch, Weilersbach (DE); Carsten Thierfelder, Pinzberg (DE); Andreas Wiesinger, Baiersdorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 248 days.

(21) Appl. No.: 15/678,217

(22) Filed: Aug. 16, 2017

(65) Prior Publication Data
US 2018/0092541 A1    Apr. 5, 2018

(30) Foreign Application Priority Data
Oct. 5, 2016  (DE) .................. 10 2016 219 276

(51) Int. Cl.
*A61B 5/00* (2006.01)
*A61B 1/07* (2006.01)
*A61B 1/00* (2006.01)

(52) U.S. Cl.
CPC .............. *A61B 5/0077* (2013.01); *A61B 1/07* (2013.01); *A61B 5/0062* (2013.01); *A61B 1/00117* (2013.01); *A61B 5/0033* (2013.01)

(58) Field of Classification Search
CPC ... A61B 5/0077; A61B 5/0062; A61B 5/0033; A61B 1/07; A61B 1/00117; A61B 6/00; A61B 6/0407; A61B 6/08; A61B 6/44
See application file for complete search history.

(56) References Cited

U.S. PATENT DOCUMENTS

| | | | | |
|---|---|---|---|---|
| 5,080,100 A | * | 1/1992 | Trotel | A61B 6/08 348/77 |
| 5,533,082 A | * | 7/1996 | Gronemeyer | A61B 6/035 378/20 |
| 6,041,249 A | | 3/2000 | Regn | |
| 6,044,291 A | * | 3/2000 | Rockseisen | A61B 6/08 378/206 |
| 2002/0141174 A1 | * | 10/2002 | Parker | A61M 21/02 362/612 |

(Continued)

FOREIGN PATENT DOCUMENTS

| | | |
|---|---|---|
| CN | 105708460 A | 6/2016 |
| DE | 4412164 A1 | 10/1995 |

(Continued)

OTHER PUBLICATIONS

Chinese Office Action and English translation thereof dated Sep. 21, 2017.

(Continued)

*Primary Examiner* — David P Porta
*Assistant Examiner* — Jeremy S Valentiner
(74) *Attorney, Agent, or Firm* — Harness, Dickey & Pierce, P.L.C.

(57) ABSTRACT

A medical imaging apparatus includes a gantry with a tunnel-shaped opening, an examination region and a holder. In an embodiment, the holder includes a light source for illuminating the examination region and the holder is arranged on the gantry projecting above the tunnel-shaped opening.

28 Claims, 4 Drawing Sheets

(56) References Cited

U.S. PATENT DOCUMENTS

| | | | | |
|---|---|---|---|---|
| 2008/0002426 A1* | 1/2008 | Vayser | ................. | A61B 1/0623 362/574 |
| 2011/0082348 A1* | 4/2011 | Herold | ................. | A61B 5/055 600/249 |
| 2015/0196367 A1* | 7/2015 | Muller | ................. | A61B 6/032 600/410 |
| 2016/0174914 A1* | 6/2016 | Lerch | ................. | A61B 6/0407 5/601 |

FOREIGN PATENT DOCUMENTS

| | | | | |
|---|---|---|---|---|
| DE | 19801446 A1 | 9/1998 | | |
| DE | 19718686 A1 | 11/1998 | | |
| DE | 4202302 C2 | 6/1999 | | |
| DE | 102012220599 A1 * | 5/2014 | .............. | A61B 6/08 |
| DE | 102014226467 A1 | 6/2016 | | |
| JP | H1099318 A | 4/1998 | | |

OTHER PUBLICATIONS

Onjukka, E. et al; "Does Prostate Radiation Therapy Treatment Planning Benefit From MRI?"; in Lax International Journal of Radiation Oncology; vol. 93; No. 3S; Poster Viewing Session E569; Supplement 2015.

Dowling, Jason A.; "An Atlas-Based Electron Density Mapping Method for Magnetic Resonance Imaging (MRI)—Alone Treatment Planning and Adaptive MRI-Based Prostate Radiation Therapy"; in: International Journal of Radiation Oncology, 2012, vol. 83, No. 1, pp. 5-11.

Torrado-Carvajal, Angel et al; "Fast Patch-Based Pseudo-CT Synthesis from T1-Weighted MR Images for PET/MR Attenuation Correction in Brain Studies"; in The Journal of Nuclear Medicine; vol. 57; No. 1; pp. 136-143, Jan. 2016.

Albrecht, Moritz H. et al; "Assessment of an Advanced Monoenergetic Reconstruction Technique in Dual-Energy Computed Tomography of Head and Neck Cancer"; in Eur Radiol; European Society of Radiology 2015; DOI 10.1007/500330-015-3627-1.

Greer, Peter B. et al; "A magnetic resonance imaging-based workflow for planning radiation therapy for prostate cancer"; in MJA; vol. 194; No. 4; pp. S24-527; Feb. 21, 2011.

Hsu, Shu-Hui et al; "Investigation of a method for generating synthetic CT models from MRI scans of the head and neck for radiation therapy"; in: Phys Med Biol.; vol. 58; No. 23; Dec. 7, 2013; DOI:10.1088/0031-9155/58/23/8419.

Jonsson, Joakim H. et al: "Treatment planning of intracranial targets on MRI derived substitute CT data"; In Radiotherapy and Oncology; No. 108; pp. 118-122; (2013).

German Office Action dated May 26, 2017.

* cited by examiner

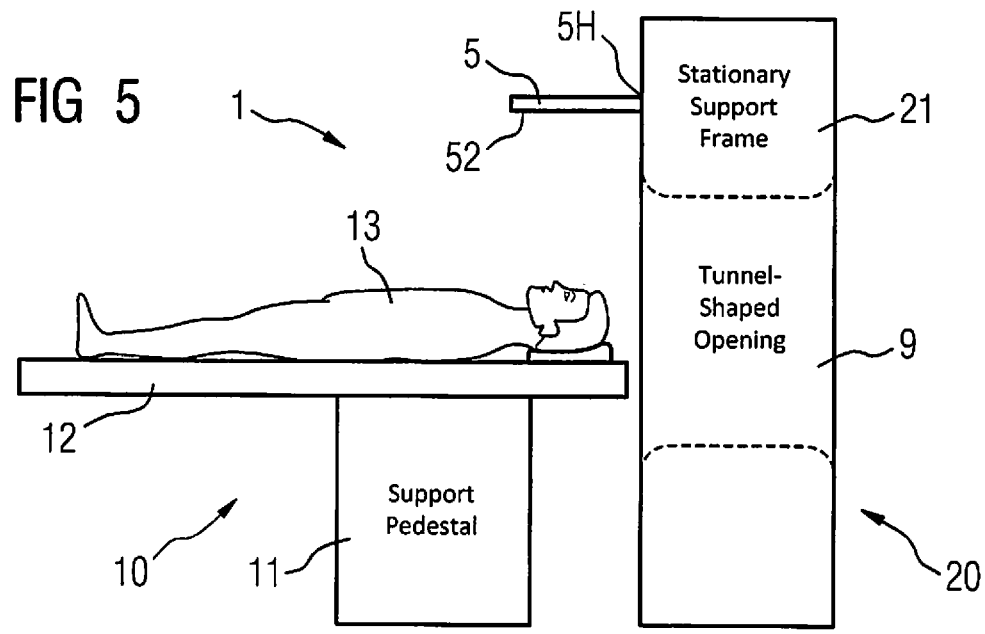
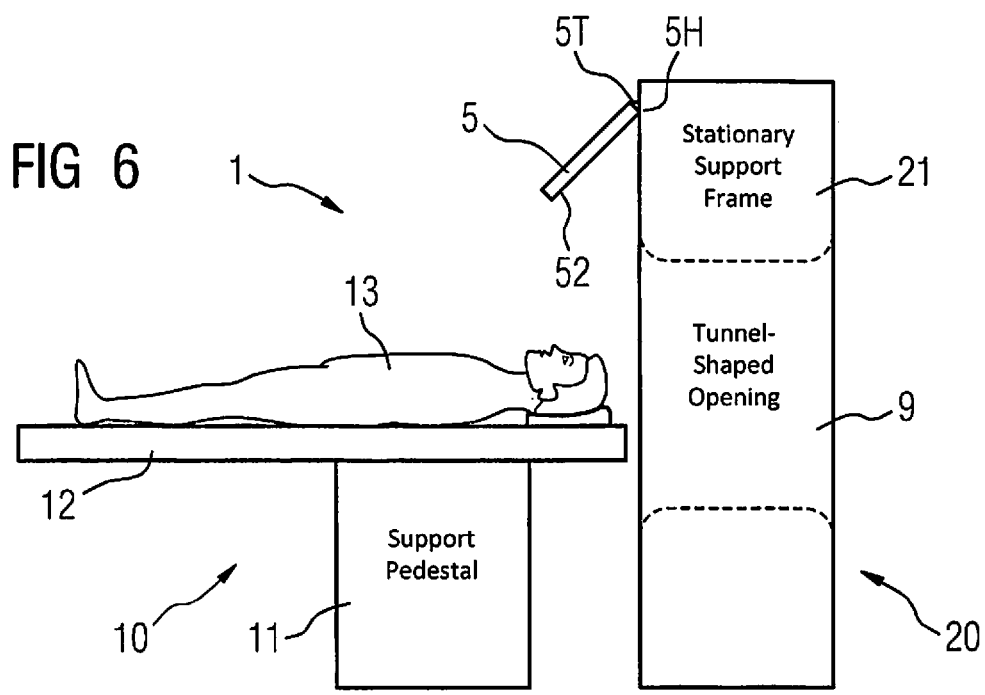

MEDICAL IMAGING APPARATUS WITH A LIGHT SOURCE FOR ILLUMINATING AN EXAMINATION REGION

PRIORITY STATEMENT

The present application hereby claims priority under 35 U.S.C. § 119 to German patent application number DE 102016219276.0 filed Oct. 5, 2016, the entire contents of which are hereby incorporated herein by reference.

FIELD

At least one embodiment of the invention generally relates to a medical imaging apparatus comprising a gantry with a tunnel-shaped opening, an examination region and/or a holder comprising a light source.

BACKGROUND

To improve workflow on medical imaging apparatuses, it is important for components used in the preparation and/or assistance of an examination via the medical imaging apparatus to be arranged as advantageously as possible relative to an examination region of the medical imaging apparatus. Examples of such components include a camera, in particular for patient observation and/or for patient positioning, and/or a display apparatus with which the patient can be provided with visual information.

To acquire acquisition data for a region to be depicted of the patient, the patient is supported on the transfer plate and introduced together with the transfer plate such that the region of the patient to be depicted is arranged in the acquisition region. Herein, the acquisition region can be covered at least from above.

In particular, the acquisition region can be formed by a tunnel-shaped opening. This results in essential requirements relating to the arrangement of the components. For example, it would be advantageous for a camera to be able to detect the patient optically, both when the patient is still supported in front of the acquisition region and when the patient has been introduced part way into the acquisition region. Conversely, if possible from the lying position, the patient should be able to see a display apparatus, both when the head is located before the acquisition region and when the head is located in the acquisition region. The advantages that can be achieved with a given arrangement of components can in particular substantially depend on the illumination of the examination region.

SUMMARY

At least one embodiment of the invention enables improved illumination of an examination region of a medical imaging apparatus.

The claims address further advantageous aspects of the invention.

At least one embodiment of the invention relates to a medical imaging apparatus comprising a gantry with a tunnel-shaped opening, an examination region and a holder, wherein the holder comprises a light source for illuminating the examination region, wherein the holder is arranged on the gantry projecting above the tunnel-shaped opening. The holder can in particular be arranged between the tunnel-shaped opening and an upper edge of the gantry with reference to a vertical direction.

At least one embodiment of the invention further relates to a medical imaging apparatus comprising a gantry with a tunnel-shaped opening, an examination region, a holder and a swivel apparatus, wherein the holder is arranged on the gantry via the swivel apparatus such that an end of the holder facing away from the gantry can be swiveled in the direction of the examination region. The holder can be in particular be arranged on the gantry projecting above the tunnel-shaped opening.

BRIEF DESCRIPTION OF THE DRAWINGS

The following explains selected embodiments with reference to the attached figures. The depiction in the figures is schematic, greatly simplified and not necessarily true to scale.

The figures show.

DETAILED DESCRIPTION OF THE EXAMPLE EMBODIMENTS

Figure 1:
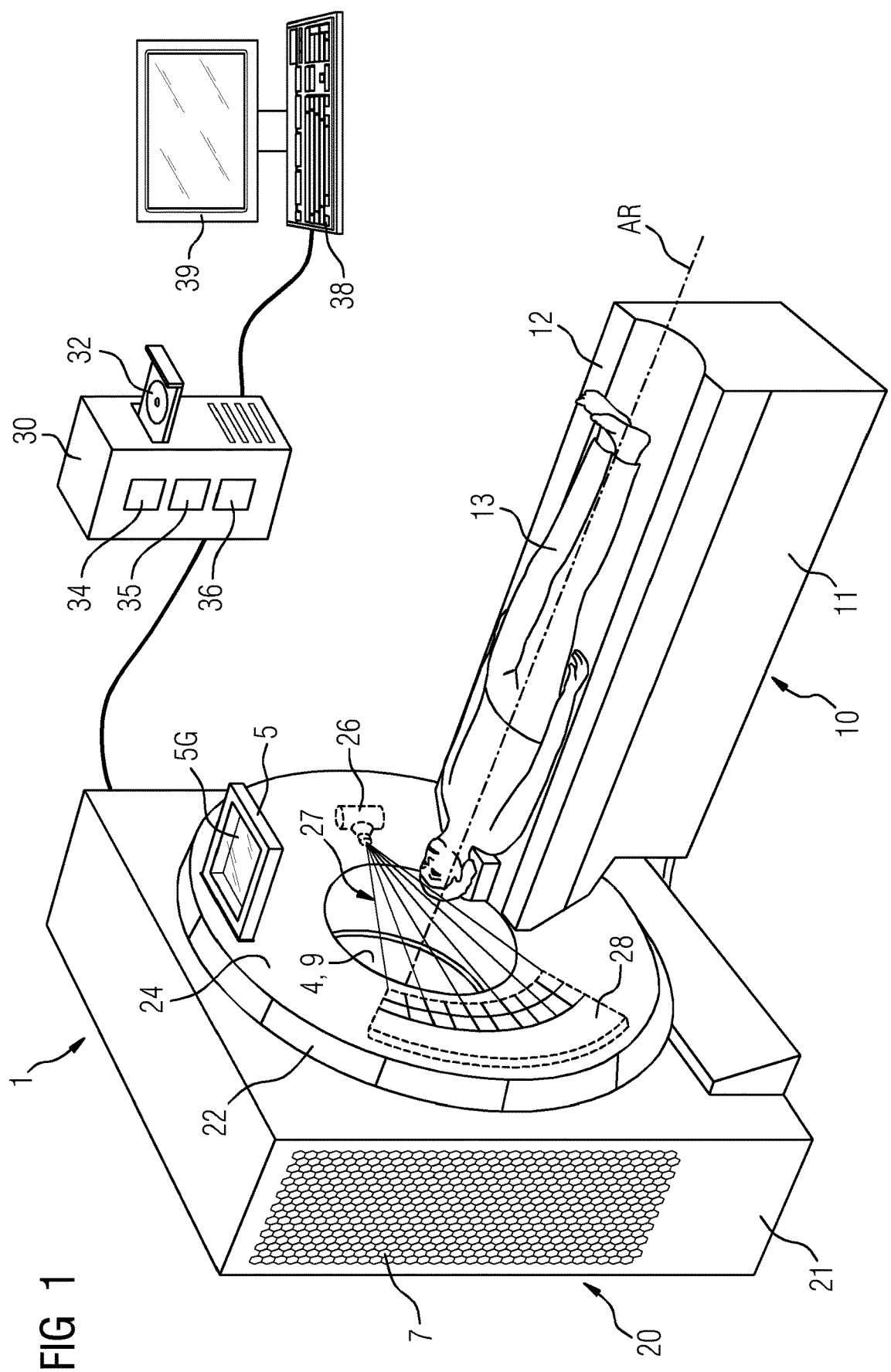
FIG. 1 a medical imaging apparatus according to a first embodiment of the invention, FIG. 2 the medical imaging apparatus shown in FIG. 1 in another depiction, FIG. 3 the holder of the medical imaging apparatus according to the first embodiment of the invention in a first view, FIG. 4 the holder of the medical imaging apparatus according to the first embodiment of the invention in a second view, FIG. 5 a medical imaging apparatus according to a second embodiment of the invention in a first operating state, FIG. 6 the medical imaging apparatus according to the second embodiment of the invention in a second operating state.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a medical imaging apparatus comprising a gantry with a tunnel-shaped opening, an examination region and a holder, wherein the holder comprises a light source for illuminating the examination region, wherein the holder is arranged on the gantry projecting above the tunnel-shaped opening. The holder can in particular be arranged between the tunnel-shaped opening and an upper edge of the gantry with reference to a vertical direction.

At least one embodiment of the invention further relates to a medical imaging apparatus comprising a gantry with a tunnel-shaped opening, an examination region, a holder and a swivel apparatus, wherein the holder is arranged on the gantry via the swivel apparatus such that an end of the holder facing away from the gantry can be swiveled in the direction of the examination region. The holder can be in particular be arranged on the gantry projecting above the tunnel-shaped opening.

The examination region can in particular include at least one region of the tunnel-shaped opening and/or at least one region of the acquisition region. The light source can in particular be spaced apart from the gantry such that the at least one region of the tunnel-shaped opening can be directly illuminated via the light source. Herein it is not necessary for it to be possible for each region of the light source to illuminate a region of the tunnel-shaped opening. The at least one region of the tunnel-shaped opening can in particular be directly illuminated via the light source when the at least one region of the tunnel-shaped opening can be directly illuminated via at least one region of the light source.

The medical imaging apparatus can in particular comprises a patient support apparatus with a support table and a transfer plate for supporting a patient, wherein the transfer plate is arranged movably on the support table relative to the support table such that the transfer plate can be introduced in a longitudinal direction of the transfer plate into the tunnel-shaped opening. The examination region can in particular include at least one region of the patient support apparatus and/or at least one region of a patient support region.

The examination region can in particular be located within a spatial region, which is defined by the medical imaging apparatus, in particular by the gantry and/or the patient support apparatus. In particular, the examination region can at least include a region located outside the tunnel-shaped opening. In such a region located outside the tunnel-shaped opening, a patient supported on the patient support apparatus can be prepared, in particular by medical staff, for an examination via the medical imaging apparatus, for example by the application of EKG electrodes.

The patient support region is a spatial region provided to support the patient. In particular, the patient support region can be connected vertically to the patient support apparatus, for example to the transfer plate. In particular, the patient support region can be at least partially spatially defined by the patient support apparatus and/or a supported patient lying on the patient support apparatus. In particular, the patient can be supported lying at least in a part of the patient support region.

The light source can in particular comprise a fiber-optic conductor arrangement and a light-coupling unit with which light can be coupled into the fiber-optic conductor arrangement. The fiber-optic conductor arrangement can in particular be embodied to decouple the light in the direction of the examination region.

The fiber-optic conductor arrangement can in particular be embodied as flat. The light-coupling unit can in particular be arranged about a circumference of the fiber-optic conductor arrangement. In particular, it can be possible for the light-coupling unit to couple the light into the fiber-optic conductor arrangement such that the light is substantially propagated perpendicular to a surface normal of the fiber-optic conductor arrangement in the fiber-optic conductor arrangement. The fiber-optic conductor arrangement can in particular comprise a disk made of light-conducting material and/or at least one light-decoupling element. The at least one light-decoupling element can in particular be embodied to decouple the light from the disk made of light-conducting material. The at least one light-decoupling element can in particular comprise an etching and/or an engraving.

The holder can in particular comprise a frame element. The light-coupling unit can in particular be arranged on the frame element. In particular, at least one region of the fiber-optic conductor arrangement can be bordered by the frame element. In particular, the fiber-optic conductor arrangement can be bordered and/or framed by the frame element. The frame element can in particular be embodied as circumferentially closed and/or be arranged about the circumference of the fiber-optic conductor arrangement.

The medical imaging apparatus can in particular comprise a swivel apparatus, wherein the holder is arranged on the gantry via the swivel apparatus such that an end of the holder facing away from the gantry can be swiveled in the direction of the examination region. The swivel apparatus can in particular comprise a clamping apparatus. The clamping apparatus can in particular be embodied, on the swiveling of the end of the holder facing away from the gantry, to absorb mechanical stress in the direction of the examination region.

The holder can in particular comprise a data-transmission module and/or a control module. The data-transmission module can in particular be embodied to receive control data. The control module can in particular be embodied to control the light source based on the control data.

The holder can in particular be embodied to arrange at least one component relative to the examination region. The at least one component can in particular be selected from the group consisting of a camera, a projection facility, an illumination apparatus, a display apparatus, an input apparatus, a microphone, a loudspeaker, an interface for the transmission of data and/or power, a holding apparatus, a rail guidance, a support arm and combinations thereof.

The holder can in particular be arranged to arrange a camera relative to the examination region. The camera can in particular be spaced apart from the gantry such that the at least one region of the tunnel-shaped opening, which can be directly illuminated via the light source, can be optically detected via the camera. Herein, it is not necessary for all regions of the tunnel-shaped opening that can be directly illuminated by the light source to be optically detectable via the camera.

The fiber-optic conductor arrangement can, for example, comprise a glass body, which can in particular be translucent and/or transparent. The light-conducting material can in particular be glass, for example metallic glass and/or organic glass and/or inorganic non-metallic glass. The fiber-optic conductor arrangement can in particular have a layer structure with a plurality of layers. For example, the fiber-optic conductor arrangement can comprise a first layer and a second layer. The first layer can in particular be embodied to conduct the light coupled into the first layer by the light-coupling unit and to decouple the light into the second layer. The second layer can in particular be embodied for volume scattering of the light decoupled from the first layer into the second layer. This enables a uniform flat distribution of the intensity of the light decoupled out of the fiber-optic conductor arrangement to be achieved. According to a further embodiment of the invention, the fiber-optic conductor arrangement can comprise a layer embodied both to conduct the light coupled into the first layer by the light-coupling unit and to decouple the light in the direction of the examination region and for volume scattering of the light.

The at least one light-decoupling element can in particular have a three-dimensional structure and/or be engraved into the light-conducting material via a laser. In particular in the case of organic glass, for example acrylic glass, the at least one light-decoupling element can be implemented in the form of an etched profile.

The frame element can in particular be embodied as ring-shaped or U-shaped. The fiber-optic conductor arrangement can in particular be bordered by the frame element such that light can be coupled into the fiber-optic conductor arrangement via the light-coupling unit. The light-coupling unit can in particular comprise at least one luminous element, for example in the form of a light-emitting diode, which can, for example, be arranged between the frame element and the fiber-optic conductor arrangement and/or an a region of the frame element facing the fiber-optic conductor arrangement.

The light-coupling unit can in particular be embodied as ring-shaped and/or comprise a plurality of luminous elements, which can, for example, be arranged in a ring shape about a circumference of the fiber-optic conductor arrangement. The light-coupling unit can in particular be embodied to couple in light such that the light in the fiber-optic conductor arrangement has a two-dimensional and/or ambient color progression. To this end, the light-coupling unit can comprise a set of luminous elements, wherein, for each luminous element of the set of luminous elements, the color of the emitted light can be individually controlled. This enables the light source light to output light with a two-dimensional and/or ambient color progression in the direction of the examination region.

On the holder, it is in particular possible for a camera to be arranged such that the examination region, in particular the acquisition region and/or the patient support region, can be at least partially optically detected with the camera. Thus, the patient can be optically detected, both when the patient is supported on the transfer plate before or behind the medical imaging apparatus and when the patient is introduced into the acquisition region. The camera can, for example, be a 2D camera and/or a 3D camera and/or in particular be embodied for use in the context of patient positioning.

It is in particular possible for a support arm for arranging a component to be arranged on the holder. In particular, the support arm can be arranged on the holder so that it can be rotated and/or swiveled relative to the holder. Moreover, the support arm can be positioned along the holder, for example via the rail guidance. The support arm can optionally comprise one or more joints and/or one or more telescopic facilities.

The medical imaging apparatus can, for example, be selected from the imaging-modality group consisting of an X-ray device, a C-arm X-ray device, a computed tomography device scanner (CT device), a molecular imaging device (MI device), a single photon emission computed tomography device (SPECT device), a positron emission tomography device (PET device), a magnetic resonance tomography device (MR device) and combinations thereof (in particular PET-CT device and PET-MR device). The medical imaging apparatus can moreover comprise a combination of an imaging modality selected, for example, from the imaging-modality group and an irradiation modality. Herein, the irradiation modality can, for example, comprise an irradiation unit for therapeutic irradiation. Without restricting the general concept of the invention, with some of the embodiments a computed tomography device is cited as an example of a medical imaging apparatus.

According to one embodiment of the invention, the medical imaging apparatus comprises an acquisition unit embodied for the acquisition of the acquisition data. In particular, the acquisition unit can comprise a radiation source and a radiation detector. One embodiment of the invention provides that the radiation source is embodied for the emission and/or excitation of radiation, in particular electromagnetic radiation, and/or that the radiation detector is embodied for the detection of the radiation, in particular the electromagnetic radiation. The radiation can, for example, travel from the radiation source to a region to be depicted and/or, after interaction with the region to be depicted, to the radiation detector. During interaction with the region to be depicted, the radiation is modified and hence becomes a carrier of information relating to the region to be depicted. During the interaction of the radiation with the detector, the information is acquired in the form of acquisition data.

In particular with a computed tomography device and a C-arm X-ray device, the acquisition data can be projection data, the acquisition unit a projection data acquisition unit, the radiation source an X-ray source, the radiation detector an X-ray detector. The X-ray detector can in particular be a quantum-counting and/or energy-resolving X-ray detector.

In particular with a magnetic resonance tomography device, the acquisition data can be a magnetic-resonance data set, the acquisition unit a magnetic-resonance data acquisition unit, the radiation source a first radio-frequency antenna unit, the radiation detector the first radio-frequency antenna unit and/or a second radio-frequency antenna unit.

The gantry of a medical imaging apparatus typically comprises a supporting structure on which in particular components of the acquisition unit, in particular the radiation source and/or the radiation detector are arranged. The supporting structure of the gantry typically has sufficient rigidity and strength to enable the components of the acquisition unit to be arranged both relative to one another and relative to a region to be depicted in a geometry that is sufficiently defined for the imaging. With a computed tomography device, the gantry typically comprises a support frame and a rotor mounted rotatably relative to the support frame, wherein the radiation source and the radiation detector are arranged on the rotor. Optionally, the gantry can have a tilting frame mounted tiltably relative to the support frame, wherein the rotor is arranged on the tilting frame.

With a C-arm X-ray device, the gantry typically comprises a support frame and a C-arm mounted swivelably relative to the support frame, wherein the radiation source and the radiation detector are arranged on the C-arm.

With a magnetic resonance tomography device, the gantry typically comprises a support frame, on which the basic magnet and a first radio-frequency antenna unit are arranged, wherein the first radio-frequency antenna unit is embodied in the form of a body coil, which is the term known to the person skilled in the art.

In addition to the embodiments of the invention expressly described in this application, numerous further embodiments of the invention are conceivable at which the person skilled in the art can arrive without departing from the scope of the invention as specified in the claims.

The use of the indefinite article "a" or "an" does not preclude the possibility of the feature in question also being present on a multiple basis. The use of the expression "comprise" does not preclude the possibility of the terms being linked by the expression "comprise" being identical. For example, the medical imaging apparatus comprises the medical imaging apparatus. The use of the expression "unit" does not preclude the possibility of the subject matter to which the expression "unit" relates comprising a plurality of components that are spatially separated from one another.

FIG. 1 shows a medical imaging apparatus 1 according to a first embodiment of the invention.

Without restricting the general Concept of the invention, a computed tomography device is shown by way of example for the medical imaging apparatus 1. The medical imaging apparatus 1 comprises the gantry 20, the tunnel-shaped opening 9, the holder 5, the patient support apparatus 10 and the control apparatus 30.

The gantry 20 comprises the stationary support frame 21, the tilting frame 22 and the rotor 24. The tilting frame 22 is arranged tiltably on the stationary support frame 21 about a tilt axis relative to the stationary support frame 21 via a tilting support apparatus. The rotor 24 is arranged rotatably about an axis of rotation AR relative to the tilting frame 22 on the tilting frame 22 via a pivot bearing apparatus. The tilt axis is horizontal and perpendicular to the axis of rotation AR. The axis of rotation AR encloses a tilt angle with a horizontal plane. A projection of the axis of rotation AR in the horizontal plane is parallel or substantially parallel to the longitudinal direction of the transfer plate 12.

The patient 13 can be introduced into the tunnel-shaped opening 9. The acquisition region 4 is also located in the tunnel-shaped opening 9. A region of the patient 13 to be depicted can be positioned in the acquisition region 4 such that the radiation 27 can travel from the radiation source 26 to the region to be depicted can and, after interaction with the region to be depicted, travel to the radiation detector 28.

The patient support apparatus 10 comprises the support pedestal 11 and the transfer plate 12 for supporting the patient 13. The transfer plate 12 is arranged movably on the support pedestal 11 relative to the support pedestal 11 such that the transfer plate 12 can be introduced into the acquisition region 4 in a longitudinal direction of the transfer plate 12.

The medical imaging apparatus 1 is embodied for the acquisition of acquisition data based on electromagnetic radiation 27. The medical imaging apparatus 1 comprises an acquisition unit. The acquisition unit is a projection data acquisition unit with the radiation source 26, for example a X-ray source, and the detector 28, for example a X-ray detector, in particular an energy-resolving X-ray detector. The radiation source 26 is arranged on the rotor 24 and embodied for the emission of radiation 27, for example X-rays, with radiation quanta 27. The detector 28 is arranged on the rotor 24 and embodied for the detection of the radiation quanta 27. The radiation quanta 27 can travel from the radiation source 26 to the region to be depicted of the patient 13 and, after interaction with the region to be depicted, strike the detector 28. This enables the acquisition unit to acquire acquisition data of the region to be depicted in the form of projection data.

The control apparatus 30 is embodied to receive the acquisition data acquired by the acquisition unit. The control apparatus 30 is embodied to control the medical imaging apparatus 1. The control apparatus 30 comprises the data-transmission module 35, the computer-readable medium 32 and the processor system 36. The control apparatus 30 is formed by a data processing system, which comprises a computer. The data-transmission module 35 in particular enables control data to be output to the data-transmission module 5D and/or be received by the data-transmission module 5D.

The control apparatus 30 comprises the image-reconstruction facility 34. The image-reconstruction facility 34 can be used to reconstruct a medical image data set based on the acquisition data.

The medical imaging apparatus 1 comprises an input apparatus 38 and an output apparatus 39 each of which are connected to the control apparatus 30. The input apparatus 38 is embodied to input control information, for example image-reconstruction parameters, examination parameters or the like. The output apparatus 39 is in particular embodied to output control information, images and/or acoustic signals. The gantry 20 comprises ventilation openings 7 formed by a plate arrangement, wherein the plate arrangement comprises plates arranged regularly and/or at least partially overlapping. The plates can in particular each have the shape of a substantially regular hexagon. The holder 5 is arranged on the gantry 20 projecting above the tunnel-shaped opening in the direction of the patient support apparatus 10.

The holder 5 can, for example, be arranged on the stationary support frame 21 or on the tilting frame 22, in particular on a casing of the stationary support frame 21 or on a casing of the tilting frame 22. The holder 5 can in particular be arranged with reference to a vertical direction between the tunnel-shaped opening 9 and a upper edge of the tilting frame 22.

According to the first embodiment of the invention, the extension of the holder 5 in a transverse direction, which is horizontal and perpendicular to the longitudinal axis of the transfer plate 12, is smaller than the diameter of the tunnel-shaped opening 9. The holder 5 is arranged relative to the transverse direction, which is horizontal and perpendicular to the longitudinal direction of the transfer plate 12, in a region defined by the tunnel-shaped opening 9. According to a further embodiment of the invention, the holder can extend relative to the transverse direction on one side or on both sides beyond the region defined by the tunnel-shaped opening.

The examination region includes at least one region of the tunnel-shaped opening 9 and at least one region of the patient support apparatus 10.

The fiber-optic conductor arrangement 5G is spaced apart from the gantry 20 by the holder such that the at least one region of the tunnel-shaped opening 9 can be directly illuminated via the fiber-optic conductor arrangement 5G.

Figure 2:
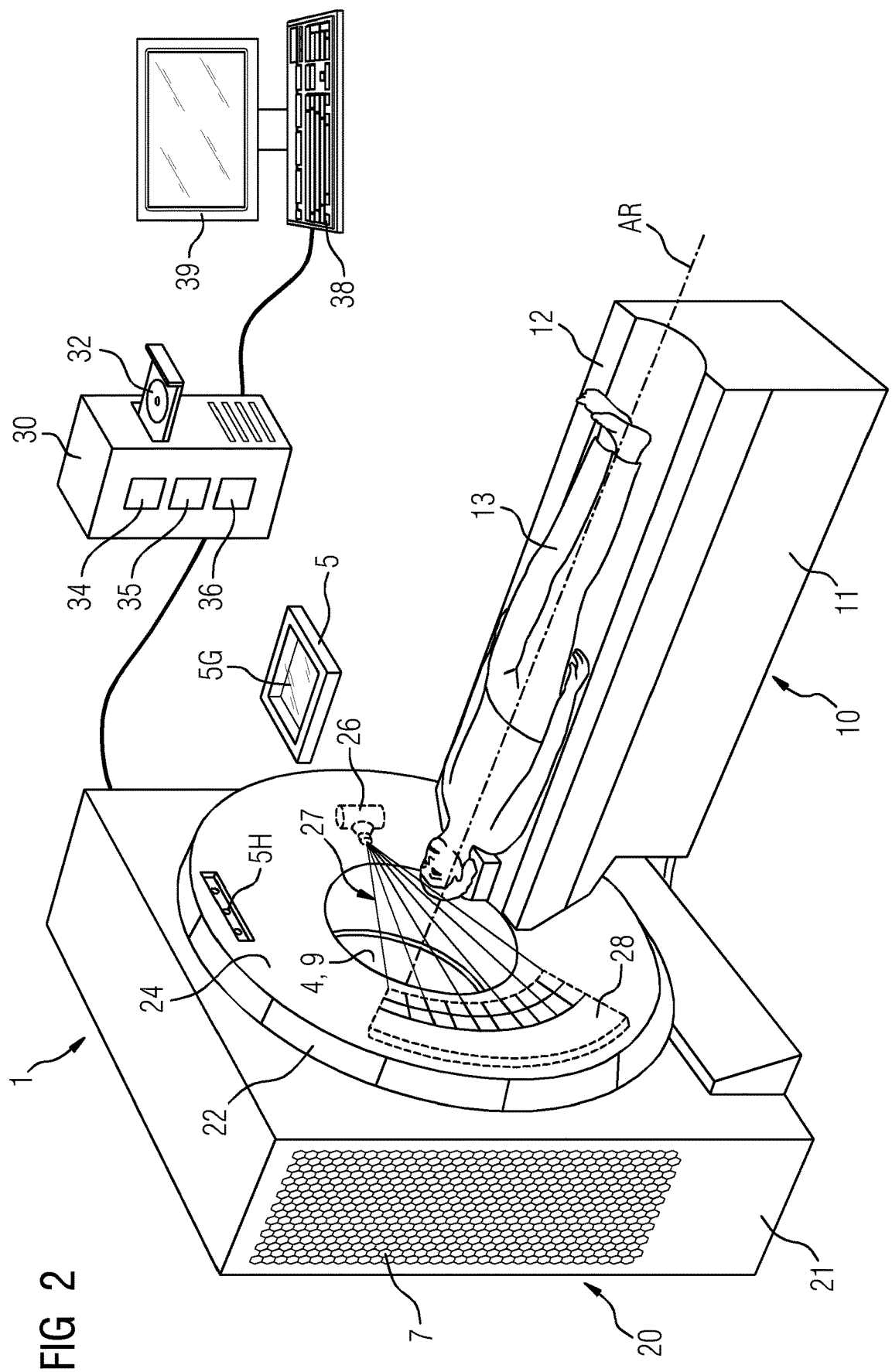

FIG. 2 is another depiction of the medical imaging apparatus 1 shown in FIG. 1 in which the holder 5 is shown separately from the gantry 20. The gantry 20 comprises a receiving unit 5H embodied to receive the holder 5. The receiving unit 5H in each case comprises a corresponding connecting element for each of the connecting elements 55, 56, 57.

According to a further embodiment of the invention, it is provided that the frame element is embodied in a U shape with a first limb, a second limb and an apex region arranged between the first limb and the second limb and/or that the receiving unit for receiving the holder comprises two receiving regions, that are each embodied to receive one of the two limbs of the frame element and/or are spaced apart from one another by a spacing between the two limbs of the frame element.

The receiving unit 5H is arranged on the casing of the gantry 20. In particular, the receiving unit 5H is arranged on a surface of the casing of the gantry 20, which faces the patient support apparatus 10 and the surface normal of which is parallel to the longitudinal direction of the transfer plate 12 parallel. In particular, the receiving unit 5H can be screwed to the casing of the gantry 20. In particular, the holder 5 can be received in the receiving unit 5H parallel to the longitudinal direction of the transfer plate 12.

Figure 3:
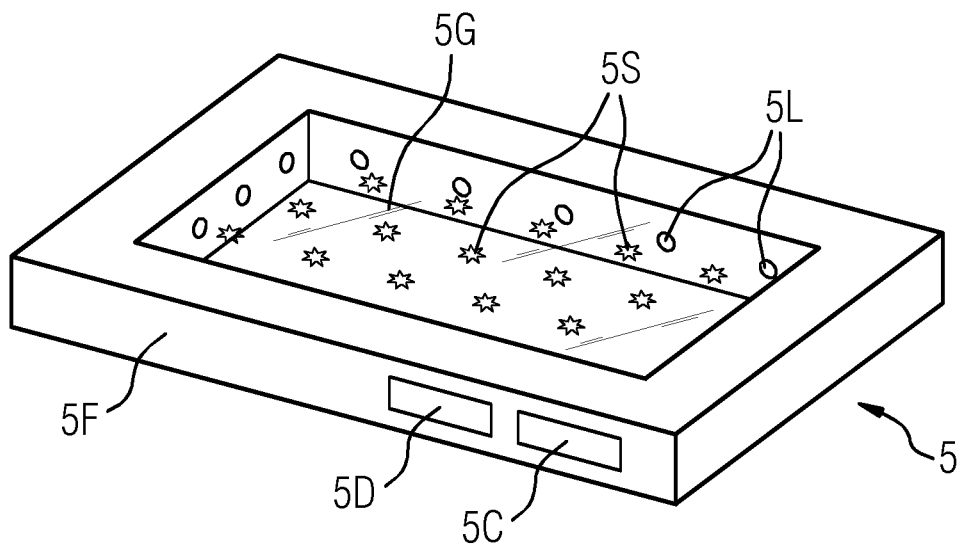

FIG. 3 shows the holder 5 of the medical imaging apparatus 1 according to the first embodiment of the invention in a first view. The first view corresponds to the view of an observer looking at the holder arranged on the gantry 20 from above. The holder 5 comprises the following components:
- the frame element 5F,
- the fiber-optic conductor arrangement 5G with a disk made of light-conducting material and light-decoupling elements 5S,
- the light-coupling unit 5L with light-emitting diodes arranged in a ring shape about a circumference of the disk made of light-conducting material.

The fiber-optic conductor arrangement 5G is embodied as flat and in particular has a surface normal that is substantially vertical and/or directed at the examination region. The fiber-optic conductor arrangement 5G comprises in particular in the longitudinal direction of the transfer plate 12 an extension of at least 10 centimeters, preferably at least 20 centimeters, and/or in a transverse direction, which is horizontal and perpendicular to the longitudinal direction of the transfer plate 12, an extension of at least 10 centimeters, preferably at least 20 centimeters.

The frame element 5F comprises a first limb 5Z1, a second limb 5Z2, a first apex region 5X1 and a second apex region 5X2. The first apex region 5X1 is connected to the second apex region 5X2 via both first limb 5Z1 and via the second limb 5Z2. The first limb 5Z1 and the second limb 5Z2 lie opposite one another in respect of the fiber-optic conductor arrangement 5G. The first apex region 5X1 and the second apex region 5X2 lie opposite one another in respect of the fiber-optic conductor arrangement 5G.

The first limb 5Z1 and the second limb 5Z2 are located in different half spaces in respect of a vertical plane in which the axis of rotation AR is located. The first apex region 5X1 is arranged between the first limb 5Z1 and the second limb 5Z2. The second apex region 5X2 is arranged between the first limb 5Z1 and the second limb 5Z2.

At least one segment of the first limb 5Z1 and at least one segment of the second limb 5Z2 are arranged relative to the longitudinal direction of the transfer plate 12 between the first apex region 5X1 and the tunnel-shaped opening 9, in particular between the first apex region 5X1 and the gantry 20.

At least one segment of the first apex region 5X1 is arranged relative to a transverse direction, which is horizontal and perpendicular to the longitudinal direction of the transfer plate 12, in a region defined by the transfer plate 12.

The first apex region 5X1 is arranged above the patient support apparatus 10, in particular such that a base point of a vertical projection of the first apex region 5X1 is located in the region of the patient support apparatus 10, for example in the region of the transfer plate 12. The first apex region 5X1 is located at an end of the holder 5 facing away from the gantry 20. The second apex region 5X2 is connected to the gantry 20 above the tunnel-shaped opening 9 and is located at one end of the holder 5, which is arranged on the gantry 20.

In this way, the solution according to the invention in particular enables an improved arrangement the light source and/or at least one further component relative to the examination region. In each case, the holder 5 comprises an extension both in the longitudinal direction of the transfer plate 12 and in a transverse direction, which is horizontal and perpendicular to the longitudinal direction of the transfer plate 12. This enables components that receive optical signals, in particular light, and/or acoustic signals, in particular voice, from the examination region and/or output the signals to the examination region to be arranged advantageously relative to the examination region via the holder 5.

The holder 5 further comprises the data-transmission module 5D and the control module 5C, which is located in an internal space formed by the casing 5V of the frame element 5F. The light source and/or the at least one component, for example the display apparatus 5Y, can in particular be controlled via the control apparatus 30 and/or via a mobile control unit, for example via a tablet computer in that control data are output via the control apparatus 30 and/or via the mobile control unit and received via the data-transmission module 5D. The control data can in particular be transmitted in a cableless and/or cable-bound fashion to and/or from the data-transmission module 5D. Cable-bound data transmission can, for example, take place via one or more of the connecting elements 55, 56, 57.

The holder 5 further comprises a display apparatus 5Y. The display apparatus 5Y can, for example, be a touch-sensitive screen and/or a strip-type light-emitting diode arrangement with which a status of the examination can be displayed. The display apparatus 5Y is arranged such that the display apparatus 5Y can be seen from the examination region.

Figure 4:
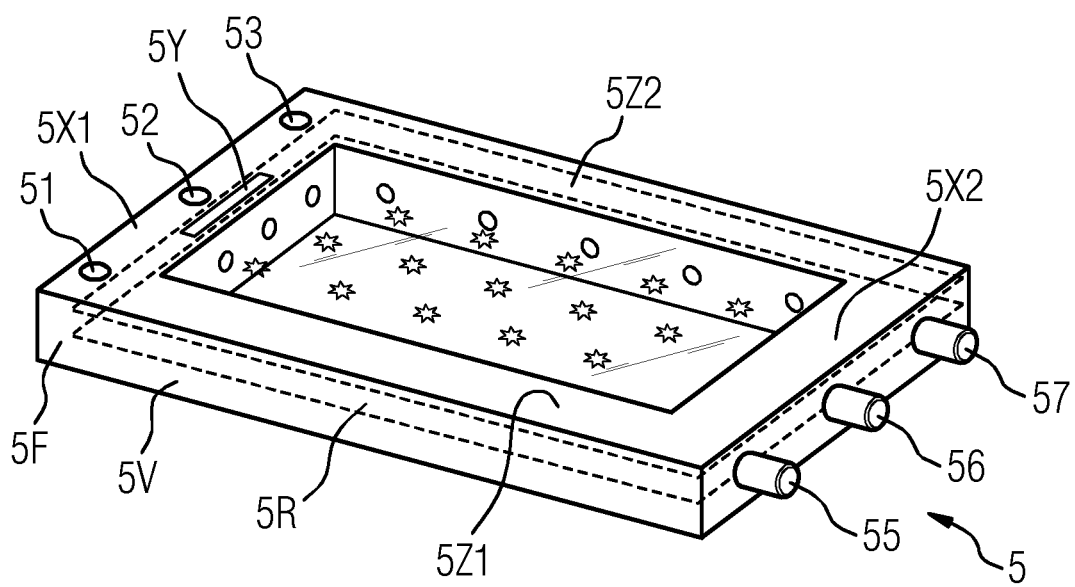

FIG. 4 shows the holder 5 of the medical imaging apparatus 1 according to the first embodiment of the invention in a second view. The second view corresponds the view of an observer from below onto the holder 5 arranged on the gantry 20. The frame element 5F comprises a casing 5V and a supporting structure 5R.

In FIG. 4, the supporting structure 5R is depicted by dashed lines and is located in an internal space of the frame element 5F bounded by the casing. The supporting structure 5R has a higher strength and/or rigidity than the casing. The casing is arranged on the supporting structure 5R such that at least some of the forces and/or moments acting on the casing 5V are routed to the supporting structure 5R. The casing 5V can in particular be embodied such that the stability of the frame element 5F is effected entirely or to a substantial degree by the casing 5V. It is in particular possible to implement embodiments of the invention with a self-supporting casing and/or with which no further supporting structure additional to the self-supporting casing is provided.

The connecting elements 55, 56, 57 located in the second apex region can in particular be used to establish a mechanical connection and/or a power transmission connection between the holder 5 and the gantry 20. In particular, the frame element 5F, in particular the supporting structure 5R, can be connected to the gantry 20 via one or more of the connecting elements 55, 56, 57. The holder 5 is in particular embodied to arrange the components 51, 52, 53 relative to the examination region.

The components 51, 52 and 53 are located in the first apex region. The components 51 and 53 can in particular be an audio interface with a microphone and/or a loudspeaker, a laser projection apparatus for projecting information onto the patient support apparatus 10 and/or onto the patient 13, a holding apparatus for infusion bags or the like. The component 52 can in particular be a camera, for example a 2D camera and/or a 3D camera. The component 52 is arranged on an end of the holder 5 facing away from the gantry 20. The component 52 is spaced apart from the gantry 20 by the holder 5 such that the at least one region of the tunnel-shaped opening 9, which can be directly illuminated via the light source, can be optically detected via the component 52.

FIG. 5 shows a medical imaging apparatus 1 according to a second embodiment of the invention in a first operating state. FIG. 6 shows the medical imaging apparatus 1 according to the second embodiment of the invention in a second operating state. According to the second embodiment of the invention, the medical imaging apparatus 1 comprises a swivel apparatus 5T with a clamping apparatus in the form of a spring mechanism. The holder 5 is arranged on the gantry 20 via the swivel apparatus 5T such that an end of the holder 5 facing away from the gantry 20 can be swiveled in the direction of the examination region. The end of the holder 5 facing away from the gantry 20 lies opposite the end of the holder 5 arranged on the gantry 20.

The clamping apparatus is embodied, on the swiveling of the end of the holder 5 facing away from the gantry 20, to absorb mechanical stress in the direction of the examination region. The clamping apparatus can in particular counteract a deflection of the holder 5 from an initial position, which is shown for example in FIG. 5. In particular, the holder 5 with the mechanical stress absorbed by the clamping apparatus can be moved back into the initial position, in particular away from the examination region.

This enables the prevention of damage to the gantry 20 and/or the holder 5 in the case of unintended loading on the holder 5. Unintentional loading on the gantry 20 can, for example, result from a patient 13 holding onto the holder 5 to assist in standing up from the transfer plate. In such a case, the patient 13 would pull the end of the holder 5 facing away from gantry 20 toward the patient, in particular in the direction of the examination region.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical imaging apparatus, comprising:
a gantry including a tunnel-shaped opening;
an examination region; and
a holder including a light source to illuminate the examination region, the holder arranged on the gantry and projecting from a surface of the gantry above the tunnel-shaped opening, wherein the light source includes a fiber-optic conductor arrangement and a light-coupling unit to couple light into the fiber-optic conductor arrangement; and
the fiber-optic conductor arrangement is configured to decouple the light in a direction of the examination region, and wherein
the holder comprises a frame element surrounding the fiber-optic conductor arrangement; and
the light-coupling unit is arranged throughout the frame element.

2. The medical imaging apparatus of claim 1, wherein at least one of
the examination region includes at least one region of the tunnel-shaped opening; and
the light source is spaced apart from the gantry such that the at least one region of the tunnel-shaped opening is directly illuminateable via the light source.

3. The medical imaging apparatus of claim 2, further comprising a patient support apparatus including a support table and a transfer plate, the transfer plate being arranged on the support table and relatively movable to the support table such that the transfer plate is introduceable into the tunnel-shaped opening in a longitudinal direction of the transfer plate, wherein the examination region includes at least one region of the patient support apparatus.

4. The medical imaging apparatus of claim 2, wherein at least one of
the light source comprises a fiber-optic conductor arrangement and a light-coupling unit to couple light into the fiber-optic conductor arrangement; and
the fiber-optic conductor arrangement is configured to decouple the light in a direction of the examination region.

5. The medical imaging apparatus of claim 4, wherein at least one of
the fiber-optic conductor arrangement is flat; and
the light-coupling unit is arranged about a circumference of the fiber-optic conductor arrangement.

6. The medical imaging apparatus of claim 4, wherein at least one of
the fiber-optic conductor arrangement comprises a disk made of light-conducting material; and
the fiber-optic conductor arrangement comprises at least one light-decoupling element configured to decouple the light from the disk made of light-conducting material.

7. The medical imaging apparatus of claim 6, wherein the at least one light-decoupling element comprises at least one of an etching and an engraving.

8. The medical imaging apparatus of claim 1, further comprising a patient support apparatus including a support table and a transfer plate, the transfer plate being arranged on the support table and relatively movable to the support table such that the transfer plate is introduceable into the tunnel-shaped opening in a longitudinal direction of the transfer plate, wherein the examination region includes at least one region of the patient support apparatus.

9. The medical imaging apparatus of claim 8, wherein at least one of
the light source comprises a fiber-optic conductor arrangement and a light-coupling unit to couple light into the fiber-optic conductor arrangement; and
the fiber-optic conductor arrangement is configured to decouple the light in the direction of the examination region.

10. The medical imaging apparatus of claim 9, wherein at least one of
the fiber-optic conductor arrangement is flat; and
the light-coupling unit is arranged about a circumference of the fiber-optic conductor arrangement.

11. The medical imaging apparatus of claim 9, wherein at least one of
the fiber-optic conductor arrangement comprises a disk made of light-conducting material; and
the fiber-optic conductor arrangement comprises at least one light-decoupling element configured to decouple the light from the disk made of light-conducting material.

12. The medical imaging apparatus of claim 11, wherein the at least one light-decoupling element comprises at least one of an etching and an engraving.

13. The medical imaging apparatus of claim 1, wherein at least one of
the fiber-optic conductor arrangement is flat; and
the light-coupling unit is arranged about a circumference of the fiber-optic conductor arrangement.

14. The medical imaging apparatus of claim 1, wherein at least one of
the fiber-optic conductor arrangement comprises a disk made of light-conducting material; and
the fiber-optic conductor arrangement comprises at least one light-decoupling element configured to decouple the light from the disk made of light-conducting material.

15. The medical imaging apparatus of claim 14, wherein the at least one light-decoupling element comprises at least one of an etching and an engraving.

16. The medical imaging apparatus of claim 1, further comprising a swivel apparatus, wherein the holder is arranged on the gantry via the swivel apparatus such that an end of the holder facing away from the gantry is swivelable in a direction of the examination region.

17. The medical imaging apparatus of claim 16, wherein the swivel apparatus comprises a clamping apparatus, and wherein the clamping apparatus is configured, on the swiveling of the end of the holder facing away from the gantry, to absorb mechanical stress in the direction of the examination region.

18. The medical imaging apparatus of claim 1, wherein
the holder includes a data-transmission module and a control module in an internal space formed by a frame element of the holder,
the data-transmission module is configured to receive control data, and
the control module is configured to control the light source based on the control data.

19. The medical imaging apparatus of claim 1, wherein
the holder is configured to arrange at least one component relative to the examination region; and
the at least one component is selected from the group consisting of a camera, a projection facility, a display apparatus, an input apparatus, a microphone, a loudspeaker, an interface for transmission of at least one of data and power, a holding apparatus, a rail guidance, and a support arm.

20. The medical imaging apparatus of claim 1, wherein the holder is arranged so as to arrange a camera relative to the examination region, and wherein the camera is spaced apart from the gantry such that at least one region of the tunnel-shaped opening, directly illuminateable via the light source, is optically detectable via the camera.

21. A medical imaging apparatus, comprising:
a gantry including a tunnel-shaped opening;
an examination region;
a holder; and
a swivel apparatus, the holder arranged via the swivel apparatus on the gantry such that an end of the holder facing away from the gantry is swivelable in a direction of the examination region, wherein the holder includes a light source having a fiber-optic conductor arrangement and a light-coupling unit to couple light into the fiber-optic conductor arrangement; and
the fiber-optic conductor arrangement is configured to decouple the light in a direction of the examination region, and wherein
the holder comprises a frame element surrounding the fiber-optic conductor arrangement; and
the light-coupling unit is arranged throughout the frame element.

22. The medical imaging apparatus of claim 21, wherein the holder is arranged on the gantry, projecting above the tunnel-shaped opening.

23. The medical imaging apparatus of claim 22, further comprising a patient support apparatus including a support table and a transfer plate, the transfer plate being arranged on the support table and being movable relative to the support table such that the transfer plate is introduceable into the tunnel-shaped opening in a longitudinal direction of the transfer plate, wherein the examination region includes at least one region of the patient support apparatus.

24. The medical imaging apparatus of claim 22, wherein the swivel apparatus includes a clamping apparatus, and wherein the clamping apparatus is configured, on the swiveling of the end of the holder facing away from the gantry, to absorb mechanical stress in the direction of the examination region.

25. The medical imaging apparatus of claim 22, wherein the holder is configured to arrange at least one component relative to an examination region, and wherein the at least one component is selected from the group consisting of a camera, a projection facility, a display apparatus, an input apparatus, a microphone, a loudspeaker, an interface for transmission of data and power, a holding apparatus, a rail guidance, and a support arm.

26. The medical imaging apparatus of claim 21, further comprising a patient support apparatus including a support table and a transfer plate, the transfer plate being arranged on the support table and being movable relative to the support table such that the transfer plate is introduceable into the tunnel-shaped opening in a longitudinal direction of the transfer plate, wherein the examination region includes at least one region of the patient support apparatus.

27. The medical imaging apparatus of claim 21, wherein the swivel apparatus includes a clamping apparatus, and wherein the clamping apparatus is configured, on the swiveling of the end of the holder facing away from the gantry, to absorb mechanical stress in the direction of the examination region.

28. The medical imaging apparatus of claim 21, wherein the holder is configured to arrange at least one component relative to an examination region, and wherein the at least one component is selected from the group consisting of a camera, a projection facility, a display apparatus, an input apparatus, a microphone, a loudspeaker, an interface for transmission of data and power, a holding apparatus, a rail guidance, and a support arm.

* * * * *